US009080195B2

(12) United States Patent
O'Brien et al.

(10) Patent No.: US 9,080,195 B2
(45) Date of Patent: Jul. 14, 2015

(54) HIGH TITER PRODUCTION OF POLY (α 1,3 GLUCAN)

(75) Inventors: John P O'Brien, Oxford, PA (US); Mark S Payne, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 182 days.

(21) Appl. No.: 13/606,400

(22) Filed: Sep. 7, 2012

(65) Prior Publication Data
US 2013/0244288 A1 Sep. 19, 2013

Related U.S. Application Data

(60) Provisional application No. 61/532,714, filed on Sep. 9, 2011.

(51) Int. Cl.
*C12P 19/18* (2006.01)
*C12N 9/00* (2006.01)
*C12N 1/20* (2006.01)
*C12N 15/00* (2006.01)
*C07H 21/04* (2006.01)
*C12P 19/04* (2006.01)

(52) U.S. Cl.
CPC ............. *C12P 19/18* (2013.01); *C12P 19/04* (2013.01); *C12Y 204/01005* (2013.01)

(58) Field of Classification Search
None
See application file for complete search history.

(56) References Cited

U.S. PATENT DOCUMENTS

| 4,501,886 A | 2/1985 | O'Brien |
| 7,000,000 B1 | 2/2006 | O'Brien |

FOREIGN PATENT DOCUMENTS

| WO | 9940217 A1 | 8/1999 |
| WO | 2010024887 A1 | 3/2010 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
International Search Report, Corresponding PCT International Application No. PCT/US2012/054521, Mailed Nov. 28, 2012.
Cote et al., the Formation of α-D-(1->3) Branch Linkages by an Exocellular Glucansucrase From Leuconostoc Mesenteroides NRRL B-742, Carbohydrate Research ,vol. 119 (1983), pp. 141-156.
Linardos et al., Monoclonal Antibody Production in Dialyzed Continuous Suspension Culture, Biotechnology and Bioengineering, Wiley & Sons, Hoboken, NJ. US, Vol. 39, No. 5 (1992) pp. 504-510.
Nakamura et al., Fractionation and Anti-Tumor Activity of the Mycelia of Liquid-Cultured *Phellinus linteus*, Biosci. Biotechnol. Biochem., vol. 68, No. 4 (2004), pp. 868-872.
Ogawa et al., Crystal Structure of (1->3)-α-D-Glucan, Fiber Differentiation Methods, vol. 47 (1980), pp. 353-362.
Simpson et al., Four Glucosyltransferases, GTFJ, GTFK, GTFL and GTFM, From *Streptococcus salivarious* ATCC 25975, Microbiology, vol. 141 (1995), pp. 1451-1460.

* cited by examiner

*Primary Examiner* — Christian Fronda

(57) ABSTRACT

A process for enzymatic preparation of poly (α1, 3 glucan) from sucrose is disclosed. The glucosyltransferase enzyme (gtfJ) from *Streptococcus salivarius* is used to convert sucrose to fructose and poly (α1, 3 glucan). Application of semi-permeable membranes to continuously remove fructose, a by-product of the gtf enzyme, thus increasing the poly (α1, 3 glucan) liter, is disclosed.

10 Claims, No Drawings

SEQUENCE LISTING

<160> NUMBER OF SEQ ID NOS: 3

<210> SEQ ID NO 1
<211> LENGTH: 4434
<212> TYPE: DNA
<213> ORGANISM: artificial sequence
<220> FEATURE:
<223> OTHER INFORMATION: codon-optimized gtfj gene from Streptococcus
      salivarius

<400> SEQUENCE: 1

```
atggacgaaa cgcaggataa gaccgtgacg cagagcaaca gcggcaccac cgcttccctg     60
gtcactagcc ctgaagccac gaaagaggcg gacaaacgca cgaacactaa agaggccgac    120
gttctgacgc ctgcaaaaga aacgaacgca gtcgagactg cgaccaccac taacacccag    180
gcgacggcgg aggccgccac gaccgcgacc accgcggacg tcgcggtggc tgcggtgccg    240
aacaaagaag cggtcgttac cacggatgct ccggcggtca cgaccgagaa agcggaagaa    300
cagccggcta ccgttaaagc agaagtcgtc aatacggaag tgaaagcgcc ggaagcggct    360
ctgaaagaca gcgaggttga ggcagcgctg agcctgaaga acatcaagaa cattgatggc    420
aagtattact atgttaatga ggatggcagc cacaaagaga atttcgctat taccgtgaat    480
ggccagctgc tgtactttgg taaagacggt gcgctgacgt cctctagcac gtattctttt    540
accccaggca ctaccaatat cgtggacggt tttagcatta caaccgcgc ttacgacagc    600 agcgaggcga gctttgagct gatcgacggt tacttgaccg cagacagctg gtatcgtccg    660
gctagcatca tcaaagatgg tgttacgtgg caagcgtcca ccgccgagga tttcgtccg    720 ctgctgatgg catggtggcc gaatgtggat acgcaggtga actatttgaa ttacatgtcc    780 aaagtttttca acctggacgc gaaatactct agcaccgaca acaggaaac cctgaaagtg    840 gcagcaaaag acattcaaat caagattgaa caaagattc aagcggagaa gagcacgcag    900
tggctgcgtg aaactatcag cgccttgtg aaacccagc gcagtggaa caaagaaacc    960 gagaattaca gcagggtgg tggtgaggac cacctgcaag gtggcgcact gctgtatgtt   1020
aacgacagcc gtacccttg ggcgaatagc gattaccgtc gtctgaatcg caccgcaacc   1080
```

```
aatcagacgg gcacgatcga taagtctatt ctggacgagc agtctgaccc aaaccacatg    1140
ggcggtttcg actttctgct ggcgaacgac gtcgacctga gcaatccggt cgtgcaggct    1200
gagcagctga atcaaatcca ctatctgatg aattggggtt ccattgtgat gggtgacaag    1260
gatgcgaact ttgacggcat tcgtgtcgat gcagttgaca acgtggacgc ggacatgttg    1320
caactgtata ccaattactt ccgtgagtac tacggtgtga acaagagcga agctaacgca    1380
ctggctcaca tcagcgttct ggaggcgtgg agcctgaatg ataatcatta caatgacaag    1440
accgatggtg cggcactggc aatggagaat aagcaacgtc tggcgctgtt gttttcgttg    1500
gcgaaaccga tcaaagagcg taccccggca gtgagcccgc tgtataacaa caccttcaat    1560
accacccagc gtgatgaaaa gaccgattgg attaacaaag acggtagcaa ggcttacaac    1620
gaagatggca cggtcaaaca atcgaccatc ggtaagtaca acgagaaata cggtgacgca    1680
tccggtaact acgttttcat ccgtgcccac gataacaacg tccaggacat catcgccgag    1740
atcatcaaga aagagatcaa cccgaaaagc gacggcttca ccatcaccga cgccgaaatg    1800
aagcaagcct ttgaaatcta taacaaagat atgctgtcga gcgacaaaaa gtataccctg    1860
aataacattc cggcagcgta tgccgtgatg ttgcagaata tggaaacgat tacccgcgtc    1920
tattacggtg atctgtatac ggacgacggt cactacatgg aaaccaaatc tccgtattac    1980
gataccatcg tgaatttgat gaagagccgt atcaagtatg tttcgggtgg ccaggcgcaa    2040
cgtagctatt ggctgccgac cgacggtaag atggacaata gcgacgttga gctgtaccgc    2100
acgaatgagg tttacacgag cgtgcgctat ggtaaggata tcatgaccgc taatgatacc    2160
gaaggctcta agtattcccg caccagcggc caagtcacct tggtcgcgaa caatccgaag    2220
ctgaatctgg accaaagcgc caagttgaat gtggagatgg gcaaaatcca tgcgaatcag    2280
aagtatcgcg cactgattgt cggcactgcg gacggcatta agaactttac ttccgacgcg    2340
gacgccattg cagcgggtta tgtgaaagaa accgatagca acggcgtgct gaccttcggt    2400
gctaacgaca ttaagggcta cgaaacgttt gatatgagcg gtttcgtggc ggtgtgggtt    2460
ccggtgggtg catctgacaa tcaggacatt cgtgttgcgc cgagcaccga ggcaaagaaa    2520
gaaggtgagc tgaccttgaa ggcgacggaa gcgtatgata ccagctgat ttacgaaggc    2580 tttagcaatt ccagacgat cccagatggc agcgatccgt ccgtgtatac gaaccgcaag    2640
attgcggaga acgtggatct gttcaaaagc tggggtgtca ccagctttga gatggcaccg    2700
caatttgtct cggcggatga tggcaccttt ctggatagcg ttattcagaa tggctacgcc    2760
ttcgccgacc gttatgacct ggccatgtcc aagaacaaca gtatggtag caaagaggac    2820 ctgcgtgatg cactgaaagc actgcataag gcgggtattc aagctatcgc agactgggtt    2880
ccagaccaga tctaccagct gccgggcaaa gaagttgtca ccgccacccg tacggatggt    2940
gctggccgta agatcgcaga cgcgattatc gaccattctc tgtatgttgc aaacagcaaa    3000
agcagcggca agattatca gcaaagtac ggtggcgagt tcctggccga gctgaaagcc    3060
aaatacccgg aaatgttcaa agttaacatg attagcacgg gtaagccgat tgatgactcc    3120
gtgaaattga gcaatggaa agccgagtac ttcaatggca ccaacgtttt ggaacgtggt    3180
gtcggctatg ttctgagcga cgaggcgacc ggtaagtatt tcacggtgac caaagaaggc    3240
aatttcattc cgctgcaact gacgggtaaa gagaaagtta tcacgggttt ctccagcgat    3300
ggtaagggta tcacctattt cggtacgagc ggtacgcagg cgaagtctgc gtttgttacc    3360
ttcaatggta acacctacta tttcgacgcg cgtggccaca tggttaccaa tagcgaatac    3420
```

-continued

| | |
|---|---|
| agcccgaatg gcaaggacgt ctaccgtttt ctgccgaacg gtatcatgct gagcaatgcg | 3480 |
| ttttacattg atgcgaacgg taatacctac ctgtacaact ctaagggtca aatgtacaaa | 3540 |
| ggcggttaca cgaaattcga tgtttctgaa acggataagg acggtaaaga gtccaaggtc | 3600 |
| gtcaagttcc gctactttac gaacgaaggc gtcatggcca agggtgttac cgtcattgat | 3660 |
| ggttttaccc aatacttcgg tgaggacggc tttcaagcga aggataagct ggtcaccttc | 3720 |
| aagggcaaga cgtattactt cgacgcacac actggtaatg gtatcaaaga tacctggcgc | 3780 |
| aatatcaatg gtaaatggta ctatttcgac gcgaatggcg ttgctgcgac cggtgcgcag | 3840 |
| gtgattaacg gccagaaact gtacttcaac gaggatggct cccaagtcaa aggcggcgtg | 3900 |
| gttaagaacg cagacggcac ctatagcaaa tacaaagaag gttttggtga gctggttact | 3960 |
| aacgagtttt tcacgactga tggcaatgtt tggtactacg ccggtgcaaa tggtaaaacc | 4020 |
| gttaccggtg cacaagtgat caacggccaa catttgtact tcaatgcgga cggttcccag | 4080 |
| gtgaagggtg gcgttgtcaa gaacgcggat ggcacctaca gcaagtacaa tgctagcact | 4140 |
| ggtgaacgtc tgacgaacga gttctttacg accggtgata caattggta ttacattggc | 4200 |
| gcaaacggta gagcgtgac gggtgaggtc aagattggtg atgatactta ctttttcgcg | 4260 |
| aaggatggca aacaagttaa aggtcaaacc gtcagcgccg gtaatggtcg cattagctac | 4320 |
| tactacggtg acagcggcaa gcgtgcggtt agcacctgga ttgagattca gccgggtgtt | 4380 |
| tatgtgtatt tcgacaaaaa cggtttggcg taccctccgc gtgttctgaa ttaa | 4434 |

<210> SEQ ID NO 2
<211> LENGTH: 8455
<212> TYPE: DNA
<213> ORGANISM: artificial sequence
<220> FEATURE:
<223> OTHER INFORMATION: plasmid pMP52

<400> SEQUENCE: 2

| | |
|---|---|
| ctcatgacca aaatccctta acgtgagtta cgcgcgcgtc gttccactga gcgtcagacc | 60 |
| ccgtagaaaa gatcaaagga tcttcttgag atcctttttt tctgcgcgta atctgctgct | 120 |
| tgcaaacaaa aaaaccaccg ctaccagcgg tggtttgttt gccggatcaa gagctaccaa | 180 |
| ctctttttcc gaaggtaact ggcttcagca gagcgcagat accaaatact gttcttctag | 240 |
| tgtagccgta gttagcccac cacttcaaga actctgtagc accgcctaca tacctcgctc | 300 |
| tgctaatcct gttaccagtg ctgctgccag tggcgataa gtcgtgtctt accgggttgg | 360 |
| actcaagacg atagttaccg gataaggcgc agcggtcggg ctgaacgggg ggttcgtgca | 420 |
| cacagcccag cttggagcga acgacctaca ccgaactgag atacctacag cgtgagctat | 480 |
| gagaaagcgc cacgcttccc gaagggagaa aggcggacag gtatccggta agcggcaggg | 540 |
| tcggaacagg agagcgcacg agggagcttc caggggaaa cgcctggtat ctttatagtc | 600 |
| ctgtcgggtt tcgccacctc tgacttgagc gtcgattttt gtgatgctcg tcagggggc | 660 |
| ggagcctatg gaaaaacgcc agcaacgcgg cctttttacg gttcctggcc ttttgctggc | 720 |
| cttttgctca catgttcttt cctgcgttat ccctgattc tgtggataac cgtattaccg | 780 |
| cctttgagtg agctgatacc gctcgccgca gccgaacgac cgagcgcagc gagtcagtga | 840 |
| gcgaggaagc ggaaggcgag agtagggaac tgccaggcat caaactaagc agaaggcccc | 900 |
| tgacggatgg cctttttgcg tttctacaaa ctctttctgt gttgtaaaac gacggccagt | 960 |
| cttaagctcg ggcccctgg gcggttctga taacagtaa tcgttaatcc gcaaataacg | 1020 |
| taaaaacccg cttcggcggg tttttttatg gggggagttt agggaaagag catttgtcag | 1080 |

```
aatatttaag ggcgcctgtc actttgcttg atatatgaga attatttaac cttataaatg    1140
agaaaaaagc aacgcacttt aaataagata cgttgctttt tcgattgatg aacacctata    1200
attaaactat tcatctatta tttatgattt tttgtatata caatatttct agtttgttaa    1260
agagaattaa gaaataaat ctcgaaaata ataaagggaa aatcagtttt tgatatcaaa    1320
attatacatg tcaacgataa tacaaaatat aatacaaact ataagatgtt atcagtattt    1380
attatgcatt tagaataaat tttgtgtcgc ccttaattgt gagcggataa caattacgag    1440
cttcatgcac agtgaaatca tgaaaaattt atttgctttg tgagcggata acaattataa    1500
tatgtggaat tgtgagcgct cacaattcca aacggtttc cctctagaaa taattttgtt    1560
taacttttga attctctaga ggaaggtaaa acatatggac gaaacgcagg ataagaccgt    1620
gacgcagagc aacagcggca ccaccgcttc cctggtcact agccctgaag ccacgaaaga    1680
ggcggacaaa cgcacgaaca ctaaagaggc cgacgttctg acgcctgcaa agaaacgaa    1740 cgcagtcgag actgcgacca ccactaacac ccaggcgacg gcgaggccg ccacgaccgc    1800 gaccaccgcg gacgtcgcgg tggctgcggt gccgaacaaa gaagcggtcg ttaccacgga    1860
tgctccggcg gtcacgaccg agaaagcgga agaacagccg gctaccgtta aagcagaagt    1920
cgtcaatacg gaagtgaaag cgccggaagc ggctctgaaa gacagcgagg ttgaggcagc    1980
gctgagcctg aagaacatca agaacattga tggcaagtat tactatgtta atgaggatgg    2040
cagccacaaa gagaatttcg ctattaccgt gaatggccag ctgctgtact ttggtaaaga    2100
cggtgcgctg acgtcctcta gcacgtattc ttttaccccca ggcactacca atatcgtgga    2160
cggttttagc attaacaacc gcgcttacga cagcagcgag gcgagctttg agctgatcga    2220
cggttacttg accgcagaca gctggtatcg tccggctagc atcatcaaag atggtgttac    2280
gtggcaagcg tccaccgccg aggattttcg tccgctgctg atggcatggt ggccgaatgt    2340
ggatacgcag gtgaactatt tgaattacat gtccaaagtt ttcaacctgg acgcgaaata    2400
ctctagcacc gacaaacagg aaaccctgaa agtggcagca aaagacattc aaatcaagat    2460
tgaacaaaag attcaagcgg agaagagcac gcagtggctg cgtgaaacta tcagcgcctt    2520
tgtgaaaacc cagccgcagt ggaacaaaga aaccgagaat tacagcaagg gtggtggtga    2580
ggaccacctg caaggtggcg cactgctgta tgttaacgac agccgtaccc cttgggcgaa    2640
tagcgattac cgtcgtctga atcgcaccgc aaccaatcag acgggcacga tcgataagtc    2700
tattctggac gagcagtctg acccaaacca catgggcggt ttcgactttc tgctggcgaa    2760
cgacgtcgac ctgagcaatc cggtcgtgca ggctgagcag ctgaatcaaa tccactatct    2820
gatgaattgg ggttccattg tgatgggtga caaggatgcg aactttgacg gcattcgtgt    2880
cgatgcagtt gacaacgtgg acgcggacat gttgcaactg tataccaatt acttccgtga    2940
gtactacggt gtgaacaaga gcgaagctaa cgcactggct cacatcagcg ttctggaggc    3000
gtggagcctg aatgataatc attacaatga caagaccgat ggtgcggcac tggcaatgga    3060
gaataagcaa cgtctggcgc tgttgttttc gttggcgaaa ccgatcaaag agcgtacccc    3120
ggcagtgagc ccgctgtata caacacctt caataccacc cagcgtgatg aaaagaccga    3180
ttggattaac aaagacggta gcaaggctta caacgaagat ggcacggtca aacaatcgac    3240
catcggtaag tacaacgaga aatacggtga cgcatccggt aactacgtttt tcatccgtgc    3300 ccacgataac aacgtccagg acatcatcgc cgagatcatc aagaaagaga tcaacccgaa    3360
aagcgacggc ttcaccatca ccgacgccga aatgaagcaa gcctttgaaa tctataacaa    3420
```

-continued

```
agatatgctg tcgagcgaca aaaagtatac cctgaataac attccggcag cgtatgccgt   3480
gatgttgcag aatatggaaa cgattacccg cgtctattac ggtgatctgt atacggacga   3540
cggtcactac atggaaacca atctccgta ttacgatacc atcgtgaatt tgatgaagag    3600
ccgtatcaag tatgtttcgg gtggccaggc gcaacgtagc tattggctgc cgaccgacgg   3660
taagatggac aatagcgacg ttgagctgta ccgcacgaat gaggtttaca cgagcgtgcg   3720
ctatggtaag gatatcatga ccgctaatga taccgaaggc tctaagtatt cccgcaccag   3780
cggccaagtc accttggtcg cgaacaatcc gaagctgaat ctggaccaaa gcgccaagtt   3840
gaatgtggag atgggcaaaa tccatgcgaa tcagaagtat cgcgcactga ttgtcggcac   3900
tgcggacggc attaagaact ttacttccga cgcggacgcc attgcagcgg gttatgtgaa   3960
agaaaccgat agcaacggcg tgctgacctt cggtgctaac gacattaagg gctacgaaac   4020
gtttgatatg agcggtttcg tggcggtgtg ggttccggtg ggtgcatctg acaatcagga   4080
cattcgtgtt gcgccgagca ccgaggcaaa gaaagaaggt gagctgacct tgaaggcgac   4140
ggaagcgtat gatagccagc tgatttacga aggctttagc aatttccaga cgatcccaga   4200
tggcagcgat ccgtccgtgt atacgaaccg caagattgcg gagaacgtgg atctgttcaa   4260
aagctggggt gtcaccagct tgagatggc accgcaattt gtctcggcgg atgatggcac    4320
ctttctggat agcgttattc agaatggcta cgccttcgcc gaccgttatg acctggccat   4380
gtccaagaac aacaagtatg gtagcaaaga ggacctgcgt gatgcactga agcactgca    4440
taaggcgggt attcaagcta cgcagactg ggttccagac cagatctacc agctgccggg    4500
caaagaagtt gtcaccgcca cccgtacgga tggtgctggc cgtaagatcg cagacgcgat   4560
tatcgaccat tctctgtatg ttgcaaacag caaaagcagc ggcaaagatt atcaagcaaa   4620
gtacggtggc gagttcctgg ccgagctgaa agccaaatac ccggaaatgt tcaaagttaa   4680
catgattagc acgggtaagc cgattgatga ctccgtgaaa ttgaagcaat ggaaagccga   4740
gtacttcaat ggcaccaacg ttttggaacg tggtgtcggc tatgttctga gcgacgaggc   4800
gaccggtaag tatttcacgg tgaccaaaga aggcaatttc attccgctgc aactgacggg   4860
taaagagaaa gttatcacgg gttttctccag cgatggtaag ggtatcacct atttcggtac   4920
gagcggtacg caggcgaagt ctgcgtttgt taccttcaat ggtaacacct actatttcga   4980
cgcgcgtggc cacatggtta ccaatagcga atacagcccg aatggcaagg acgtctaccg   5040
ttttctgccg aacggtatca tgctgagcaa tgcgtttac attgatgcga acggtaatac    5100
ctacctgtac aactctaagg gtcaaatgta caaaggcgt tacacgaaat cgatgtgttc    5160
tgaaacggat aaggacggta aagagtccaa ggtcgtcaag ttccgctact ttacgaacga   5220
aggcgtcatg gccaagggtg ttaccgtcat tgatggtttt acccaatact cggtgagga    5280
cggctttcaa gcgaaggata agctggtcac cttcaagggc aagacgtatt acttcgacgc   5340
acacactggt aatggtatca agatacctg gcgcaatatc aatggtaaat ggtactattt    5400
cgacgcgaat ggcgttgctg cgaccggtgc gcaggtgatt aacggccaga actgtacttc   5460
caacgaggat ggctcccaag tcaaaggcgg cgtggttaag aacgcagacg gcacctatag   5520
caaatacaaa gaaggttttg tgagctggt tactaacgag ttttcacga ctgatggcaa     5580
tgtttggtac tacgccggtg caaatggtaa aaccgttacc ggtgcacaag tgatcaacgg   5640
ccaacatttg tacttcaatg cggacggtc ccaggtgaag ggtggcgttg tcaagaacgc    5700
ggatggcacc tacagcaagt acaatgctag cactggtgaa cgtctgacga acgagttctt   5760
tacgaccggt gataacaatt ggtattacat tggcgcaaac ggtaagagcg tgacgggtga   5820
```

```
ggtcaagatt ggtgatgata cttactttt cgcgaaggat ggcaaacaag ttaaaggtca    5880
aaccgtcagc gccggtaatg gtcgcattag ctactactac ggtgacagcg gcaagcgtgc    5940
ggttagcacc tggattgaga ttcagccggg tgtttatgtg tatttcgaca aaaacggttt    6000
ggcgtaccct ccgcgtgttc tgaattaatg agtctagact gcagggtacc aagcttcccc    6060
aagggcgaca ccccataatt agcccgggcg aaaggcccag tctttcgact gagcctttcg    6120
ttttatttga tgcctggcag ttccctactc tcgcatgggg agtccccaca ctaccatcgg    6180
cgctacggcg tttcacttct gagttcggca tggggtcagg tgggaccacc gcgctactgc    6240
cgccaggcaa acaaggggtg ttatgagcca tattcaggta taaatgggct cgcgataatg    6300
ttcagaattg gttaattggt tgtaacactg accctatt gtttatttt ctaaatacat    6360 tcaaatatgt atccgctcat gagacaataa ccctgataaa tgcttcaata atattgaaaa    6420
aggaagaata tgagtattca acatttccgt gtcgccctta ttccctttt tgcggcattt    6480 tgccttcctg tttttgctca cccagaaacg ctggtgaaag taaaagatgc tgaagatcag    6540
ttgggtgcac gagtgggtta catcgaactg gatctcaaca gcggtaagat ccttgagagt    6600
tttcgccccg aagaacgttt tccaatgatg agcactttta agttctgct atgtggcgcg    6660 gtattatccc gtattgacgc cgggcaagag caactcggtc gccgcataca ctattctcag    6720
aatgacttgg ttgagtactc accagtcaca gaaaagcatc ttacggatgg catgacagta    6780
agagaattat gcagtgctgc cataaccatg agtgataaca ctgcggccaa cttacttctg    6840
acaacgatcg gaggaccgaa ggagctaacc gcttttttgc acaacatggg ggatcatgta    6900
actcgccttg atcgttggga accggagctg aatgaagcca taccaaacga cgagcgtgac    6960
accacgatgc ctgtagcgat ggcaacaacg ttgcgcaaac tattaactgg cgaactactt    7020
actctagctt cccggcaaca attaatagac tggatggagg cggataaagt tgcaggacca    7080
cttctgcgct cggcccttcc ggctggctgg tttattgctg ataaatccgg agccggtgag    7140
cgtggttctc gcggtatcat cgcagcgctg ggccagatg gtaagccctc ccgtatcgta    7200
gttatctaca cgacggggag tcaggcaact atggatgaac gaaatagaca gatcgctgag    7260
ataggtgcct cactgattaa gcattggtaa gcggcgcgcc atcgaatggc gcaaaacctt    7320
tcgcggtatg gcatgatagc gcccggaaga gagtcaattc agggtggtga atatgaaacc    7380
agtaacgtta tacgatgtcg cagagtatgc cggtgtctct tatcagaccg tttcccgcgt    7440
ggtgaaccag gccagccacg tttctgcgaa aacgcgggaa aaagtggaag cggcgatggc    7500
ggagctgaat tacattccca accgcgtggc acaacaactg gcgggcaaac agtcgttgct    7560
gattggcgtt gccacctcca gtctggccct gcacgcgccg tcgcaaattg tcgcggcgat    7620
taaatctcgc gccgatcaac tgggtgccag cgtggtggtg tcgatggtag aacgaagcgg    7680
cgtcgaagcc tgtaaagcgg cggtgcacaa tcttctcgcg caacgcgtca gtgggctgat    7740
cattaactat ccgctggatg accaggatgc cattgctgtg gaagctgcct gcactaatgt    7800
tccggcgtta tttcttgatg tctctgacca gacacccatc aacagtatta tttctccca    7860 tgaggacggt acgcgactgg gcgtggagca tctggtcgca ttgggtcacc agcaaatcgc    7920
gctgttagcg ggcccattaa gttctgtctc ggcgcgtctg cgtctggctg ctggcataa    7980 atatctcact cgcaatcaaa ttcagccgat agcggaacgg gaaggcgact ggagtgccat    8040
gtccggtttt caacaaacca tgcaaatgct gaatgagggc atcgttccca ctgcgatgct    8100
ggttgccaac gatcagatgg cgctgggcgc aatgcgcgcc attaccgagt ccgggctgcg    8160
```

-continued

```
cgttggtgcg gatatctcgg tagtgggata cgacgatacc gaagatagct catgttatat    8220
cccgccgtta accaccatca aacaggattt tcgcctgctg gggcaaacca gcgtggaccg    8280
cttgctgcaa ctctctcagg gccaggcggt gaagggcaat cagctgttgc cagtctcact    8340
ggtgaaaaga aaaccaccc tggcgcccaa tacgcaaacc gcctctcccc gcgcgttggc     8400
cgattcatta atgcagctgg cacgacaggt ttcccgactg gaaagcgggc agtga          8455
```

<210> SEQ ID NO 3
<211> LENGTH: 1518
<212> TYPE: PRT
<213> ORGANISM: Streptococcus salivarius

<400> SEQUENCE: 3

```
Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
                20                  25                  30

Leu Ser Val Thr Thr Ser Ser Val Ser Ala Asp Glu Thr Gln Asp Lys
            35                  40                  45

Thr Val Thr Gln Ser Asn Ser Gly Thr Thr Ala Ser Leu Val Thr Ser
        50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Ala Thr Thr Ala Thr Thr
            100                 105                 110

Ala Asp Val Ala Val Ala Val Pro Asn Lys Glu Ala Val Val Thr
        115                 120                 125

Thr Asp Ala Pro Ala Val Thr Thr Glu Lys Ala Glu Glu Gln Pro Ala
    130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Val Asn Glu Asp Gly Ser His
            180                 185                 190

Lys Glu Asn Phe Ala Ile Thr Val Asn Gly Gln Leu Leu Tyr Phe Gly
        195                 200                 205

Lys Asp Gly Ala Leu Thr Ser Ser Ser Thr Tyr Ser Phe Thr Pro Gly
    210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
            260                 265                 270

Ala Ser Thr Ala Glu Asp Phe Arg Pro Leu Leu Met Ala Trp Trp Pro
        275                 280                 285

Asn Val Asp Thr Gln Val Asn Tyr Leu Asn Tyr Met Ser Lys Val Phe
    290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
```

-continued

```
                325                 330                 335
Glu Lys Ser Thr Gln Trp Leu Arg Glu Thr Ile Ser Ala Phe Val Lys
            340                 345                 350

Thr Gln Pro Gln Trp Asn Lys Glu Thr Glu Asn Tyr Ser Lys Gly Gly
            355                 360                 365

Gly Glu Asp His Leu Gln Gly Gly Ala Leu Leu Tyr Val Asn Asp Ser
            370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
            405                 410                 415

Asp Pro Asn His Met Gly Gly Phe Asp Phe Leu Leu Ala Asn Asp Val
            420                 425                 430

Asp Leu Ser Asn Pro Val Val Gln Ala Glu Gln Leu Asn Gln Ile His
            435                 440                 445

Tyr Leu Met Asn Trp Gly Ser Ile Val Met Gly Asp Lys Asp Ala Asn
            450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
            485                 490                 495

Ser Glu Ala Asn Ala Leu Ala His Ile Ser Val Leu Glu Ala Trp Ser
            500                 505                 510

Leu Asn Asp Asn His Tyr Asn Asp Lys Thr Asp Gly Ala Ala Leu Ala
            515                 520                 525

Met Glu Asn Lys Gln Arg Leu Ala Leu Leu Phe Ser Leu Ala Lys Pro
            530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
            565                 570                 575

Ser Lys Ala Tyr Asn Glu Asp Gly Thr Val Lys Gln Ser Thr Ile Gly
            580                 585                 590

Lys Tyr Asn Glu Lys Tyr Gly Asp Ala Ser Gly Asn Tyr Val Phe Ile
            595                 600                 605

Arg Ala His Asp Asn Asn Val Gln Asp Ile Ile Ala Glu Ile Ile Lys
            610                 615                 620

Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
            645                 650                 655

Lys Lys Tyr Thr Leu Asn Asn Ile Pro Ala Ala Tyr Ala Val Met Leu
            660                 665                 670

Gln Asn Met Glu Thr Ile Thr Arg Val Tyr Tyr Gly Asp Leu Tyr Thr
            675                 680                 685

Asp Asp Gly His Tyr Met Glu Thr Lys Ser Pro Tyr Tyr Asp Thr Ile
            690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asp Asn Ser Asp
            725                 730                 735

Val Glu Leu Tyr Arg Thr Asn Glu Val Tyr Thr Ser Val Arg Tyr Gly
            740                 745                 750
```

-continued

```
Lys Asp Ile Met Thr Ala Asn Asp Thr Glu Gly Ser Lys Tyr Ser Arg
        755                 760                 765

Thr Ser Gly Gln Val Thr Leu Val Ala Asn Asn Pro Lys Leu Asn Leu
        770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
                805                 810                 815

Phe Thr Ser Asp Ala Asp Ala Ile Ala Ala Gly Tyr Val Lys Glu Thr
                820                 825                 830

Asp Ser Asn Gly Val Leu Thr Phe Gly Ala Asn Asp Ile Lys Gly Tyr
                835                 840                 845

Glu Thr Phe Asp Met Ser Gly Phe Val Ala Val Trp Val Pro Val Gly
        850                 855                 860

Ala Ser Asp Asn Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
                885                 890                 895

Leu Ile Tyr Glu Gly Phe Ser Asn Phe Gln Thr Ile Pro Asp Gly Ser
        900                 905                 910

Asp Pro Ser Val Tyr Thr Asn Arg Lys Ile Ala Glu Asn Val Asp Leu
        915                 920                 925

Phe Lys Ser Trp Gly Val Thr Ser Phe Glu Met Ala Pro Gln Phe Val
        930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
                965                 970                 975

Gly Ser Lys Glu Asp Leu Arg Asp Ala Leu Lys Ala Leu His Lys Ala
                980                 985                 990

Gly Ile Gln Ala Ile Ala Asp Trp Val Pro Asp Gln Ile Tyr Gln Leu
        995                 1000                1005

Pro Gly Lys Glu Val Val Thr Ala Thr Arg Thr Asp Gly Ala Gly
        1010                1015                1020

Arg Lys Ile Ala Asp Ala Ile Ile Asp His Ser Leu Tyr Val Ala
        1025                1030                1035

Asn Ser Lys Ser Ser Gly Lys Asp Tyr Gln Ala Lys Tyr Gly Gly
        1040                1045                1050

Glu Phe Leu Ala Glu Leu Lys Ala Lys Tyr Pro Glu Met Phe Lys
        1055                1060                1065

Val Asn Met Ile Ser Thr Gly Lys Pro Ile Asp Asp Ser Val Lys
        1070                1075                1080

Leu Lys Gln Trp Lys Ala Glu Tyr Phe Asn Gly Thr Asn Val Leu
        1085                1090                1095

Glu Arg Gly Val Gly Tyr Val Leu Ser Asp Glu Ala Thr Gly Lys
        1100                1105                1110

Tyr Phe Thr Val Thr Lys Glu Gly Asn Phe Ile Pro Leu Gln Leu
        1115                1120                1125

Thr Gly Lys Glu Lys Val Ile Thr Gly Phe Ser Ser Asp Gly Lys
        1130                1135                1140

Gly Ile Thr Tyr Phe Gly Thr Ser Gly Thr Gln Ala Lys Ser Ala
        1145                1150                1155
```

```
Phe Val Thr Phe Asn Gly Asn Thr Tyr Tyr Phe Asp Ala Arg Gly
1160                1165                1170

His Met Val Thr Asn Ser Glu Tyr Ser Pro Asn Gly Lys Asp Val
1175                1180                1185

Tyr Arg Phe Leu Pro Asn Gly Ile Met Leu Ser Asn Ala Phe Tyr
1190                1195                1200

Ile Asp Ala Asn Gly Asn Thr Tyr Leu Tyr Asn Ser Lys Gly Gln
1205                1210                1215

Met Tyr Lys Gly Gly Tyr Thr Lys Phe Asp Val Ser Glu Thr Asp
1220                1225                1230

Lys Asp Gly Lys Glu Ser Lys Val Val Lys Phe Arg Tyr Phe Thr
1235                1240                1245

Asn Glu Gly Val Met Ala Lys Gly Val Thr Val Ile Asp Gly Phe
1250                1255                1260

Thr Gln Tyr Phe Gly Glu Asp Gly Phe Gln Ala Lys Asp Lys Leu
1265                1270                1275

Val Thr Phe Lys Gly Lys Thr Tyr Tyr Phe Asp Ala His Thr Gly
1280                1285                1290

Asn Gly Ile Lys Asp Thr Trp Arg Asn Ile Asn Gly Lys Trp Tyr
1295                1300                1305

Tyr Phe Asp Ala Asn Gly Val Ala Ala Thr Gly Ala Gln Val Ile
1310                1315                1320

Asn Gly Gln Lys Leu Tyr Phe Asn Glu Asp Gly Ser Gln Val Lys
1325                1330                1335

Gly Gly Val Val Lys Asn Ala Asp Gly Thr Tyr Ser Lys Tyr Lys
1340                1345                1350

Glu Gly Phe Gly Glu Leu Val Thr Asn Glu Phe Phe Thr Thr Asp
1355                1360                1365

Gly Asn Val Trp Tyr Tyr Ala Gly Ala Asn Gly Lys Thr Val Thr
1370                1375                1380

Gly Ala Gln Val Ile Asn Gly Gln His Leu Tyr Phe Asn Ala Asp
1385                1390                1395

Gly Ser Gln Val Lys Gly Gly Val Val Lys Asn Ala Asp Gly Thr
1400                1405                1410

Tyr Ser Lys Tyr Asn Ala Ser Thr Gly Glu Arg Leu Thr Asn Glu
1415                1420                1425

Phe Phe Thr Thr Gly Asp Asn Asn Trp Tyr Tyr Ile Gly Ala Asn
1430                1435                1440

Gly Lys Ser Val Thr Gly Glu Val Lys Ile Gly Asp Asp Thr Tyr
1445                1450                1455

Phe Phe Ala Lys Asp Gly Lys Gln Val Lys Gly Gln Thr Val Ser
1460                1465                1470

Ala Gly Asn Gly Arg Ile Ser Tyr Tyr Tyr Gly Asp Ser Gly Lys
1475                1480                1485

Arg Ala Val Ser Thr Trp Ile Glu Ile Gln Pro Gly Val Tyr Val
1490                1495                1500

Tyr Phe Asp Lys Asn Gly Leu Ala Tyr Pro Pro Arg Val Leu Asn
1505                1510                1515
```

HIGH TITER PRODUCTION OF POLY (α 1,3 GLUCAN)

This application claims priority to the provisional application U.S. 61/532,714 and the provisional application U.S. 61/532,720 both filed on Sep. 9, 2011.

FIELD OF INVENTION

This invention relates to the field of production of a structural polysaccharide. Specifically, it relates to production of poly (α1, 3 glucan) via an enzymatic reaction. More specifically, it relates to increasing the titer of poly (α1, 3 glucan) formed during the enzymatic reaction.

BACKGROUND

Cellulose, a polysaccharide formed from glucose via β(1, 4) glycoside linkages by natural processes (Applied Fiber Science, F. Happey, Ed., Chapter 8, E. Atkins, Academic Press, New York, 1979), has achieved commercial prominence as a fiber as a consequence of the many useful products derived therefrom. In particular, cotton, a highly pure form of naturally occurring cellulose, is well-known for its beneficial attributes in textile applications.

Cellulose exhibits sufficient chain extension and backbone rigidity in solution to form liquid crystalline solutions (U.S. Pat. No. 4,501,886). However, sufficient polysaccharide chain extension has hitherto been achieved primarily in β(1, 4) linked polysaccharides. Any significant deviation from that backbone geometry in the glucan polysaccharide family lowers the molecular aspect ratio below that required for the formation of an ordered lyotropic phase. Additionally, it is well-known that important commercial cellulosic fibers such as cotton and rayon increasingly present sustainability issues with respect to land use and environmental imprint.

It is therefore highly desirable to discover other glucose-based polysaccharides with utility in films, fibers and resins largely because of the current emphasis on producing low cost, structural materials from renewable resources. In addition such polymers offer materials that are environmentally benign throughout their entire life cycle.

Poly (α1, 3 glucan), a glucan polymer characterized by having α(1, 3) glycoside linkages, has been isolated by contacting an aqueous solution of sucrose with a glucosyltransferase (gtfJ) enzyme isolated from *Streptococcus salivarius* (Simpson et al., Microbiology, 141: 1451-1460, 1995). Glucan refers to a polysaccharide composed of D-glucose monomers linked by glycosidic bonds. Films prepared from poly (α1, 3 glucan) tolerated temperatures up to 150° C. and provided an advantage over polymers obtained from β(1, 4) linked polysaccharides (Ogawa et al., Fiber Differentiation Methods, 47: 353-362, 1980).

U.S. Pat. No. 7,000,000 disclosed preparation of a polysaccharide fiber comprising hexose units, wherein at least 50% of the hexose units within the polymer were linked via α(1, 3) glycoside linkages using the glucosyltransferase enzyme gtfJ of *Streptococcus salivarius*. The disclosed polymer formed a liquid crystalline solution when it was dissolved above a critical concentration in a solvent or in a mixture comprising a solvent. From this solution continuous, strong, cotton-like fibers, highly suitable for use in textiles, were spun and used either in a derivatized form or as a non-derivatized (regenerated) form. The poly (α1, 3 glucan) in U.S. Pat. No. 7,000,000 was made in a batch process wherein the poly (α1, 3 glucan) titers were typically less than 25 grams of poly (α1, 3 glucan) per liter of the reactor volume.

It can be desirable to develop processes to increase the titer of the poly (α1, 3 glucan) formed by the enzymatic reaction.

SUMMARY OF INVENTION

This invention is a process for production of poly (α1, 3 glucan) from a renewable feedstock, for applications in fibers, films, and pulps. The polymer is made directly in a one step enzymatic reaction using a recombinant glucosyltransferase (gtfJ) enzyme as the catalyst and sucrose as the substrate.

In one aspect, the disclosed invention is a process for producing poly (α1, 3 glucan) in a reaction system comprising two chambers separated by a semi-permeable membrane, wherein:

a) a first chamber comprises an enzyme reaction solution comprising:
  i) sucrose; and
  ii) at least one glucosyltransferase enzyme; and
b) a second chamber, separated from the first chamber by a semi-permeable membrane in contact with the enzyme reaction solution wherein the semi-permeable membrane is permeable to fructose and other low molecular weight moieties but impermeable to poly (α1, 3 glucan), facilitates continuous removal of fructose and other low molecular weight moieties while retaining poly (α1, 3 glucan) and the at least one glucosyltransferase enzyme inside the first chamber.

In another aspect, the disclosed invention is a process wherein poly (α1, 3 glucan), at a titer of 30-200 grams per liter, is produced from sucrose by at least one glucosyltransferase enzyme.

In yet another aspect, the disclosed invention is a genetically modified *Escherichia coli* that produces an active glucosyltransferase enzyme comprising a plasmid comprising a gene that is codon optimized for expression in *Escherichia coli* and is operably linked to a T5 promoter.

DESCRIPTION OF DNA SEQUENCES

SEQ NO. 1 is the DNA sequence of the synthesized gene of the mature glucosyltransferase which has been codon optimized for expression in *E. coli*.

SEQ NO. 2 is the DNA sequence for the plasmid pMP52.

SEQ NO. 3 is the amino acid sequence of the mature glucosyltransferase (gtfJ enzyme; EC 2.4.1.5; GENBANK® AAA26896.1) from *Streptococcus salivarius* (ATCC 25975).

DETAILED DESCRIPTION OF INVENTION

Poly (α1, 3 glucan) is a potentially low cost polymer which can be enzymatically produced from renewable resources such as sucrose using the gtfJ enzyme of *Streptococcus salivarius*. It has been shown that selected polymers comprising hexose units with α(1, 3) glycoside linkages can form ordered liquid crystalline solutions when the polymer is dissolved in a solvent under certain conditions (U.S. Pat. No. 7,000,000). Moreover such solutions can be spun into continuous, high strength, cotton-like fibers. In U.S. Pat. No. 7,000,000, batch enzymatic reactions were employed for conversion of sucrose to poly (α1, 3 glucan) with gtfJ, and the by-products fructose and leucrose accumulated in the reactor. Since the accumulated fructose is known to compete for glycosly moieties during enzymatic reaction, conversion of available glucose to poly (α1, 3 glucan) was subsequently hindered thus limiting the final titer of the desired product per unit reactor volume.

The term "leucrose", as used herein, refers to a disaccharide consisting of glucose and fructose, linked by an α(1, 5) bond.

The term "glucosyltransferase (gtf) enzyme", as used herein, refers to an enzyme excreted by oral streptococci, such as *Streptococcus salivarius* which utilizes the high free energy of the glycosidic bond of sucrose to synthesize poly (α1, 3 glucan). A glycosidic bond can join two monosaccharides to form a disaccharide. The glycosidic bonds can be in the α or β configuration and can generate, for example, α(1, 2), α(1, 3), α(1, 4), α(1, 6), β(1, 2), β(1, 3), β(1, 4) or β(1, 6) linkages. The term "α(1,3) glycoside linkage", as used herein, refers to a type of covalent bond that joins glucose molecules to each other through the ring carbons 1 and 3 on adjacent glucose rings.

The term "poly (α1, 3 glucan)", as used herein, refers to high molecular weight, linear polymers obtained from polysaccharide molecules resulting from linking glucose units via α(1,3) glycosidic linkages.

The present invention relates to a process for increasing the titer of the polysaccharide, poly (α1, 3 glucan), produced from sucrose in an enzymatic reaction using one or more gtf enzymes. The term "enzymatic reaction" refers to a reaction that is performed by the gtf enzyme. An "enzyme reaction solution" of the present invention generally refers to a reaction mixture comprising at least one gtf enzyme in a buffer solution comprising sucrose and possibly one or more primers to convert sucrose to poly (α1, 3 glucan).

For purposes of this invention, the gtf enzyme (E.C. 2.4.1.5) of *Streptococcus salivarius* is used.

In an embodiment, the enzyme reaction solution can comprise only one gtf enzyme as described herein. In another embodiment, the enzyme reaction solution can comprise a combination of more than one type of gtf enzyme.

For purposes of this invention, sufficient quantities of the gtfJ enzyme are produced using a recombinant *E. coli* strain for gtfJ production.

The genetically modified *Escherichia coli* suitable for the present invention comprises a plasmid comprising a gene that can be codon optimized for expression in *Escherichia coli* and can be operably linked to a promoter. The suitable promoter for this invention can be selected from but not limited to lac, trc, trp, PL, T5 or T7. In an embodiment of this invention the promoter used is the T5 promoter. The suitable *E. coli* for use in this invention can be selected from strains selected from, but not limited to MG1655, FM5, TOP10, BL21, DH5alpha. In an embodiment of this invention the *E. coli* used is strain MG1655. In another embodiment, the suitable *E. coli* strain for production of poly (α1, 3 glucan) according to the present invention is strain MG1655/pMP52.

Methods for the growth of recombinant microorganisms are well known in the art. Recombinant microorganisms expressing the desired gtf enzyme to perform the instant reaction can be grown in any container, such as, for example: various types of flasks with and without indentations; any autoclavable container that can be sealed and temperature-controlled; or any type of fermenter. In one embodiment, production of the gtfJ enzyme for poly (α1, 3 glucan) production in the present invention can be achieved by growing the recombinant *E. coli* MG1655/pMP52, expressing the gtfJ enzyme, in a fermenter.

The gtfJ enzyme of *Streptococcus salivarius*, used as the catalyst for conversion of sucrose to poly (α1, 3 glucan) in the current invention, is a primer-independent gtf enzyme. The primer-independent enzymes do not require the presence of a primer to perform the reaction. A primer-dependent gtf enzyme, as referenced in the present application, refers to a gtf enzyme that requires the presence of an initiating molecule in the enzyme reaction solution to act as a primer for the enzyme during poly (α1, 3 glucan) synthesis. Thus a "primer", as the term is used herein, refers to any molecule that can act as the initiator for the primer-dependent glycosyltransferases. For the purposes of the present invention, either or both a primer-independent enzyme, and/or a primer-dependent gtf enzyme can be used in the same enzyme reaction system during poly (α1, 3 glucan) synthesis.

While gtfJ is a primer-independent enzyme, it also performs the reaction in the presence of a primer. In the present invention, dextran, which is a complex, branched glucan was used as a primer for the gtfJ enzyme. Thus in an embodiment, the gtfJ reaction solution for production of poly (α1, 3 glucan) does not comprise a primer. Alternatively, in another embodiment, the gtfJ reaction solution for production of poly (α1, 3 glucan) comprises a primer. The presence of a primer in the gtfJ reaction solution increases production of poly (α1, 3 glucan) as shown in the Examples below.

The production of poly (α1, 3 glucan), by the gtfJ enzyme of *Streptococcus salivarius* is inhibited by its by-product, fructose. When fructose accumulates in the enzyme reaction solution it can inhibit the production of poly (α1, 3 glucan) by the enzyme, presumably by competing for available glycosyl moieties which results in the formation of the disaccharide, leucrose. In the present invention, to reduce the effect on gtfJ of fructose, the fructose in the enzyme reaction solution is continuously removed to prevent its accumulation to inhibitory levels in the enzyme reaction solution. For the purposes of the current invention in an embodiment, the reaction system comprises a semi-permeable membrane that separates the enzyme reaction solution, contained in the first chamber, comprising one or more gtf enzymes, one or more primers and sucrose, from the surrounding buffer contained in the second chamber. The term "chamber" as used herein, refers to any container that can hold the enzyme reaction solution or the products of the enzyme reaction solution. The chamber can be made of glass, plastic, metal, film, membrane or any other type of inert material that can hold the enzyme reaction solution. The term "semi-permeable membrane", as used herein, refers to a membrane that will allow passage of certain molecules or ions by diffusion while retaining some other molecules. Essentially any semi-permeable membrane, with a molecular cutoff between 12,000 and 100,000 Daltons that will allow fructose and other low molecular weight moieties to pass through while retaining the enzyme and poly (α1, 3 glucan) can be suitable for use in the present invention. The term "other low molecular weight moieties" as used herein, refers to various compounds with molecular weights below 1000 Dalton that can be present in the enzyme reaction solution. Due to the removal of the by-product fructose from the enzyme reaction solution contained in the first chamber, leucrose formation can be reduced. In one embodiment of the present invention, dialysis tubing is used as the semi-permeable membrane to remove the by-product fructose from the enzyme reaction solution.

In an embodiment of the present invention the amount of poly (α1, 3 glucan) formed in the reaction mixture using dialysis tubing is 30 g/L. In another embodiment the amount of poly (α1, 3 glucan) formed in the reaction mixture using dialysis tubing is 180 g/L.

The suitable temperature for performing the reaction according to the disclosed invention can be from 5° C. to 50° C. Alternatively, the suitable temperature can be from 20° C. to 37° C. In an embodiment, the temperature for performing the reaction according to the disclosed invention is 20-25° C. In another embodiment, the temperature for performing the reaction according to the disclosed invention is 37° C.

The present invention provides for production of poly (α1, 3 glucan), as a low cost material that can be economically obtained from readily renewable sucrose feedstock for a variety of applications including fibers, films, and pulps. In particular, it is expected that poly (α1, 3 glucan) fibers, for example, will functionally substitute for cotton and regenerated cellulose fibers, leading to new textile fibers with minimal environmental impact and excellent sustainability versus the aforementioned incumbents.

EXAMPLES

The invention is further described and illustrated in, but not limited to, the following specific embodiments.

Materials

Dialysis tubing (Spectrapor 25225-226, 12000 molecular weight cut-off) was obtained from VWR (Radnor, Pa.).

Dextran and ethanol were obtained from Sigma Aldrich. Sucrose was obtained from VWR.

Suppressor 7153 antifoam was obtained from Cognis Corporation (Cincinnati, Ohio).

All other chemicals were obtained from commonly used suppliers of such chemicals.

Abbreviations Used:

"g/L" is gram(s) per liter; "mL" is milliliter(s); "mg" is milligram(s); "mg/mL" is milligram(s) per milliliter; "mL/L" is milliliters per liter; "w/w" is weight per weight; "w/v" is weight per volume; "rpm" is revolutions per minute; "nm" is nanometers; "OD" is optical density; "mM" is millimolar; "psi" is Pounds pressure per square inch; "slpm" is standard liters per minute; "g feed/min" is grams feed per minute; "IPTG" is isopropyl β-D-1-thiogalacto-pyranoside; "kDa" is killo Dalton; "BCA" is bicinchoninic acid.

Seed Medium

The seed medium, used to grow the starter cultures for the fermenters, contained: yeast extract (Amberx 695, 5.0 grams per liter, g/L), $K_2HPO_4$ (10.0 g/L), $KH_2PO_4$ (7.0 g/L), sodium citrate dihydrate (1.0 g/L), $(NH_4)_2SO_4$ (4.0 g/L), $MgSO_4$ heptahydrate (1.0 g/L) and ferric ammonium citrate (0.10 g/L). The pH of the medium was adjusted to 6.8 using either 5N NaOH or $H_2SO_4$ and the medium was sterilized in the flask. Post sterilization additions included glucose (20 mL/L of a 50% w/w solution) and ampicillin (4 mL/L of a 25 mg/mL stock solution).

Fermenter Medium

The growth medium used in the fermenter contained: $KH_2PO_4$ (3.50 g/L), $FeSO_4$ heptahydrate (0.05 g/L), $MgSO_4$ heptahydrate (2.0 g/L), sodium citrate dihydrate (1.90 g/L), yeast extract (Ambrex 695, 5.0 g/L), Suppressor 7153 antifoam (0.25 milliliters per liter, mL/L), NaCl (1.0 g/L), $CaCl_2$ dihydrate (10 g/L), and NIT trace elements solution (10 mL/L). The NIT trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization additions included glucose (12.5 g/L of a 50% w/w solution) and ampicillin (4 mL/L of a 25 mg/mL stock solution).

Example 1

Construction of Glucosyltransferase (gtfJ) Enzyme Expression Strain

A gene encoding the mature glucosyltransferase enzyme (gtfJ; EC 2.4.1.5; GENBANK® AAA26896.1, SEQ ID NO: 3) from *Streptococcus salivarius* (ATCC 25975) was synthesized using codons optimized for expression in *E. coli* (DNA 2.0, Menlo Park Calif.). The nucleic acid product (SEQ ID NO: 1) was subcloned into pJexpress404® (DNA 2.0, Menlo Park Calif.) to generate the plasmid identified as pMP52 (SEQ ID NO: 2). The plasmid pMP52 was used to transform *E. coli* MG1655 (ATCC47076™) to generate the strain identified as MG1655/pMP52. All procedures used for construction of the glucosyltransferase enzyme expression strain are well known in the art and can be performed by individuals skilled in the relevant art without undue experimentation.

Example 2

Production of Recombinant gtfJ in Fermentation

Production of the recombinant gtfJ enzyme in a fermenter was initiated by preparing a pre-seed culture of the *E. coli* strain MG1655/pMP52, expressing the gtfJ enzyme, constructed as described in Example 1. A 10 mL aliquot of the seed medium was added into a 125 mL disposable baffled flask and was inoculated with a 1.0 mL culture of *E. coli* MG1655/pMP52 in 20% glycerol. This culture was allowed to grow at 37° C. while shaking at 300 revolutions per minute (rpm) for 3 hours.

A seed culture, for starting the fermenter, was prepared by charging a 2 L shake flask with 0.5 L of the seed medium. 1.0 mL of the pre-seed culture was aseptically transferred into 0.5 L seed medium in the flask and cultivated at 37° C. and 300 rpm for 5 hours. The seed culture was transferred at $OD_{550nm}>2$ to a 14 L fermenter (Braun, Perth Amboy, N.J.) containing 8 L of the fermenter medium described above at 37° C.

Cells of *E. coli* MG1655/pMP52 were allowed to grow in the fermenter and glucose feed (50% w/w glucose solution containing 1% w/w $MgSO_4.7H_2O$) was initiated when glucose concentration in the medium decreased to 0.5 g/L. The feed was started at 0.36 g feed/min and increased progressively each hour to 0.42, 0.49, 0.57, 0.66, 0.77, 0.90, 1.04, 1.21, 1.41 1.63, 1.92, 2.2 g feed/min respectively. The rate remained constant afterwards. Glucose concentration in the medium was monitored using an YSI glucose analyzer (YSI, Yellow Springs, Ohio). When glucose concentration exceeded 0.1 g/L the feed rate was decreased or stopped temporarily. Induction of glucosyltransferase enzyme activity was initiated, when cells reached an $OD_{550}$ of 70, with the addition of 9 mL of 0.5 M IPTG. The dissolved oxygen (DO) concentration was controlled at 25% of air saturation. The DO was controlled first by impeller agitation rate (400 to 1200 rpm) and later by aeration rate (2 to 10 slpm). The pH was controlled at 6.8. $NH_4OH$ (14.5% w/v) and $H_2SO_4$ (20% w/v) were used for pH control. The back pressure was maintained at 0.5 bars. At various intervals (20, 25 and 30 hours), 5 mL of Suppressor 7153 antifoam was added into the fermenter to suppress foaming. Cells were harvested by centrifugation 8 hours post IPTG addition and were stored at −80° C. as a cell paste.

Example 3

Preparation of gtfJ Crude Enzyme Extract from Cell Paste

The cell paste obtained above was suspended at 150 g/L in 50 mM potassium phosphate buffer pH 7.2 to prepare a slurry. The slurry was homogenized at 12,000 psi (Rannie-type machine, APV-1000 or APV 16.56) and the homogenate chilled to 4° C. With moderately vigorous stirring, 50 g of a floc solution (Aldrich no. 409138, 5% in 50 mM sodium phosphate buffer pH 7.0) was added per liter of cell homogenate. Agitation was reduced to light stirring for 15 minutes. The cell homogenate was then clarified by centrifugation at 4500 rpm for 3 hours at 5-10° C. Supernatant, containing crude gtfJ enzyme extract, was concentrated (approximately 5×) with a 30 kDa cut-off membrane. The concentration of protein in the gftJ enzyme solution was determined by the BCA protein assay (Sigma Aldrich) to be 4-8 g/L.

Example 4

Improving the Titer of Poly (α1, 3 Glucan) by Using a Semi-Permeable Membrane

This Example demonstrates that removal and/or dilution of the by-product fructose, formed during conversion of sucrose to poly (α1, 3 glucan), increases poly (α1, 3 glucan) titer. Dialysis tubing was used as a semi-permeable membrane in this Example since it allows passage of the by-product fructose formed during the enzymatic reaction, from inside the tubing to outside of the dialysis tubes.

The enzyme reaction solution in this Example contained 8 L of the sucrose stock solution (Table 1), 24 g of dextran T-10, as the primer, and 1.0 volume % of the gtf enzyme.

TABLE 1

Sucrose stock solution

| Material | concentration |
|---|---|
| Sucrose | 1200 g |
| $KH_2PO_4$ Buffer (pH 6.8-7.0) | 50 mM |
| 10% KOH sol'n | as needed for adjusting to pH 7 |
| Ethanol | 800 mL |
| De-ionized water | To 8 liters |

Four individual dialysis tubes (50 mL capacity) were used as test samples and charged with 50 mL of the enzyme reaction solution and were sealed. The individual dialysis tubes were then suspended in polyethylene buckets holding different volumes of the sucrose stock solution (Table 1) as the surrounding buffer. These polyethylene buckets were then placed on a magnetic stirring plate and allowed to stir at 20-25° C. for 72 hours. A control sample was prepared, in a capped centrifuge tube, consisting of 50 mL of the enzyme reaction solution, in the same proportions as the test samples, and allowed to stand at 20-25° C. temperature for 72 hours without stirring. The control sample was not placed in the dialysis tube or the surrounding buffer.

After 72 hours, the test samples in the dialysis tubes were removed from the surrounding buffer, the tubes were cut open and the poly (α1, 3 glucan) solids were collected on a Buchner funnel using 325 mesh screen over 40 micrometers filter paper. The filter cake was resuspended in deionized water and filtered twice more as above to remove residual sucrose, fructose and other low molecular weight, soluble by-products. Finally two additional washes with methanol were performed. The filter cake was pressed out thoroughly on the funnel and dried under vacuum at room temperature. The poly (α1, 3 glucan) formed in the control sample was also isolated and weighed. Formation of poly (α1, 3 glucan) in the tests and the control samples was confirmed using publically available information (Nakamura, T., et al., Biosci. Biotechnol. Biochem., 68: 868-872, 2004). The resulting dry weights of the poly (α1, 3 glucan) obtained following conversion of sucrose to poly (α1, 3 glucan) by the gtfJ enzyme, from the test and the control samples, are shown in Table 2.

TABLE 2

Comparison of poly (α 1, 3 glucan) formed in the presence and absence of a semi-permeable membrane

| Volume of 15% sucrose solution (the surrounding buffer) | poly (α 1, 3 glucan) (g) |
|---|---|
| 5 L | 1.395 g |
| 2.5 L | 1.515 g |
| 250 mL | 1.132 g |
| 250 mL | 1.114 g |
| Control | 0.696 g |

The above results show clearly that the titer of poly (α1, 3 glucan) was significantly enhanced when the enzyme reaction solution was placed in a dialysis tube and was placed in the surrounding buffer that allowed continuous passage of the by-product fructose from inside the dialysis tube to outside, thus diluting the concentration of fructose, formed by the enzyme, inside the tube. The highest polymer titers were obtained at higher volumes of the surrounding buffer which can result in higher dilution of the by-product fructose.

Example 5

Determination of the Amount of Poly (α1, 3 Glucan) Formed at Timed Intervals

To 3 L of the sucrose stock solution (Table 1), 9 g of dextran T-10, as the primer and 2.0% volume % of gtf were added to prepare the enzyme reaction solution.

Seven individual dialysis tubes were used as test samples and charged with 50 mL of the enzyme reaction solution and were sealed. The individual dialysis tubes were then suspended in a polyethylene bucket containing 3 L of the sucrose stock solution as the surrounding buffer. The buckets were placed on a magnetic stirring plate and allowed to stir at 20-25° C. for 72 hours. Individual dialysis tubes were removed at timed intervals shown in Table 3. Since the titer of the poly (α1, 3 glucan) formed in control samples, as described in the Example 4, was consistently around 0.6 g after 72 hours, no control samples were used in this experiment. Formation of poly (α1, 3 glucan) in the tests and the control samples was confirmed using the method described above.

At each timed interval, the poly (α1, 3 glucan) solids formed in the dialysis tubes were isolated as described in Example 4. The resulting dry weights of the poly (α1, 3 glucan) obtained enzyme reaction solution at various time intervals are shown in Table 3.

TABLE 3

Weight of the Poly (α 1, 3 glucan) formed at various timed intervals

| Time (hour) | poly (α 1, 3 glucan) (g) |
|---|---|
| 6 | 0.48 |
| 21 | 1.21 |
| 28 | 1.33 |
| 36 | 1.52 |
| 48 | 1.71 |
| 60 | 2.07 |
| 72 | 2.50 |

The above results clearly showed that production of poly (α1, 3 glucan) was significantly enhanced as the enzyme reaction was allowed to proceed for a longer period of time (e.g., 72 hours).

Example 6

Improving the Titer of Poly (α1, 3 Glucan) by Using a Semi-Permeable Membrane at Elevated Temperatures This Example demonstrates that removal and/or dilution of the by-product, fructose, formed during conversion of sucrose to poly (α1, 3 glucan), and performing the reaction at elevated temperatures can increase the poly (α1, 3 glucan) titer. Dialysis tubing was used as a semi-permeable membrane in this Example since it allows passage of the by-product fructose, formed during the enzymatic reaction, from inside the tubing to the surrounding sucrose stock outside the dialysis tubing.

Five separate test systems were set up. Three liters of a sucrose stock solution (Table 4) were prepared for each test.

TABLE 4

Sucrose stock solution

| Material | concentration |
|---|---|
| Sucrose | 1200 g |
| KH$_2$PO$_4$ Buffer (pH 6.8-7.0) | 50 mM |
| 10% KOH sol'n | as needed for adjusting to pH 7 |
| Ethanol | 800 mL |
| De-ionized water | To 8 liters |

The experiment was designed to take five samples from each test at various timed intervals (Table 5). Thus a total of 25 dialysis tubes were set up. Five tubes for the control, five tubes for test #1, five tubes for test #2, five tubes for test #3 and five tests for test #4. Each individual dialysis tube was charged with 50 mL of the stock solution containing either 1 volume percent (vol %) of gtfJ enzyme extract (control, test #1, test #3 and test #4), or 2 vol % gtfJ enzyme extract (test #2). Control and test tube #1, test tube #2 and test tube #4 contained 3 g/L of dextran as the primer. Test tubes #3 had 6 g/L of dextran. The dialysis tubes for each set of tests were then suspended in a 1 gallon-capacity polyethylene container with a screw cap top that contained 3 liters of freshly prepared sucrose stock solution, as the surrounding buffer outside the dialysis tubes, and the container was sealed. Test sample #4 did not contain any ethanol. In this assay, ethanol was used to prevent microbial contamination that can occur during lengthy enzyme incubation. Test samples #1-4 were all performed at 37° C. while the control samples were performed at 20-25° C.

At specific intervals a single dialysis tube was removed from each container, cut open and the glucan solids were collected on a Buchner funnel using 325 mesh screen over 40 micrometers filter paper. The filter cake was resuspended in deionized water and washed twice more as above to remove sucrose, fructose and other low molecular weight, soluble by-products. Finally two additional washes with methanol were carried out. The filter cake was pressed out thoroughly on the funnel and dried under vacuum at 20-25° C. The poly (α1, 3 glucan) formed in the control sample was also isolated and weighed. Formation of poly (α1, 3 glucan) was confirmed as described above. The resulting dry weights of the poly (α1, 3 glucan) obtained following conversion of sucrose to poly (α1, 3 glucan) are shown in Table 6.

TABLE 5

Composition of control and test samples for enzymatic synthesis of Poly (α 1,3 glucan)

| Material/ Condition | Amount Control | Amount test 1 | Amount test 2 | Amount test 3 | Amount test 4 |
|---|---|---|---|---|---|
| Sucrose | 450 g | 450 g | 450 g | 450 g | 450 g |
| Dextran T-10 | 3 g/L | 3 g/L | 3 g/L | 6 g/L | 3 g/L |
| KH$_2$PO$_4$ Buffer | as needed | as needed | as needed | as needed | as needed |
| 10% KOH sol'n | as needed | as needed | as needed | as needed | as needed |
| Enzyme Extract | 1 vol % | 1 vol % | 2 vol % | 1 vol % | 1 vol % |
| Ethanol | 300 mL | 300 mL | 300 mL | 300 mL | none |
| De-ionized water | as needed | as needed | as needed | as needed | as needed |
| Temperature | 20-25° C. | 37° C. | 37° C. | 37° C. | 37° C. |

TABLE 6

Weight of poly (α 1,3 Glucan) produced vs Time

| Time (hours) | Control Glucan (g) | test 1 Glucan (g) | test 2 Glucan (g) | test 3 Glucan (g) | test 4 Glucan (g) |
|---|---|---|---|---|---|
| 4 | 0.281 | 0.508 | 0.751 | 0.565 | 0.777 |
| 24 | 0.750 | 1.501 | 2.557 | 1.853 | 2.693 |
| 48 | 1.026 | 2.917 | 4.290 | 3.215 | 4.236 |
| 72 | 1.347 | 4.305 | 6.015 | 4.534 | 6.090 |
| 144 | 2.391 | 8.074 | 9.090 | 7.202 | 6.210 |

The above results clearly demonstrate that in all the tests performed the titer of Poly (α1, 3 glucan) was significantly enhanced by continuously diluting or removing the by-product fructose as it was formed during enzymatic synthesis and by performing the reaction at 37° C. In the best case (test #2) the final titer for glucan production per unit volume of the polymerization vessel (50 mL) was 6.015 g/0.05 L (or 182 g/L) at 72 hour as compared to 1.3 g/0.05 L (or 48 g/L) for the control that had been incubated at 20-25° C. temperature.

Example 7

Enzymatic Synthesis of Poly (α1, 3 Glucan) without a Primer Using a Semi-Permeable Membrane Eight liters of the sucrose stock solution, containing no dextran T-10 as the primer for the gtfJ enzyme reaction, were prepared using the ingredients as shown in Table 1.

Three individual dialysis tubes (50 mL volume) were used as test samples and charged with 50 mL of the sucrose stock solution containing 1.0 volume % crude gtfJ enzyme prepared as described above and were sealed. Thus, the final contents of each dialysis tube consisted of sucrose, dextran, crude gtfJ enzyme and potassium phosphate buffer. The individual dialysis tubes were then suspended in containers holding different volumes of the sucrose stock solution (Table 1). These containers were placed on a magnetic stirring plate and allowed to stir at 20-25° C. temperature for 72 hours with the dialysis tubes suspended within. A control sample was prepared, in a capped centrifuge tube, consisting of 50 mL of enzyme/sucrose/buffer solution, without the dextran primer, in the same proportions as the test samples, and allowed to stand at ambient temperature for 72 hours without stirring.

After 72 hours the dialysis tubes were removed, cut open and the glucan solids were collected on a Buchner funnel using 325 mesh screen over a 40 micrometer filter paper. The filter cake was resuspended in deionized water and filtered twice more as above to remove any residual sucrose, fructose and other low molecular weight, soluble by-products. Finally two additional washes with methanol were carried out. The filter cake was pressed out thoroughly on the funnel and dried under vacuum at 20-25° C. The glucan polymer prepared in the control sample was also isolated and weighed using the procedure described above. Formation of poly (α1, 3 glucan) was confirmed as described above. The resulting dry weights of the poly (α1, 3 glucan) obtained following the enzymatic conversion of sucrose to poly (α1, 3 glucan) from the test and the control samples are shown in Table 7.

TABLE 7

Glucan yields during reaction of gtfJ without the primer dextran

| Volume of 15% Sucrose Solution | Glucan Yield (g) |
|---|---|
| 5 liter | 1.26 g |
| 2.5 liter | 1.35 g |

TABLE 7-continued

Glucan yields during reaction of gtfJ without the primer dextran

| Volume of 15% Sucrose Solution | Glucan Yield (g) |
|---|---|
| 250 mL | 1.07 g |
| Control | 0.51 g |

The above results show clearly that the gtfJ enzyme has functioned in the absence of the primer, as a primer-independent enzyme. The control indicates production of poly (α1, 3 glucan) in the absence of the primer while the by-product fructose, formed during the reaction, accumulates and limits production of poly (α1, 3 glucan). On the other hand, in the three test reactions that were performed in the dialysis tubes and the by-product of the reaction, fructose, was continuously diluted higher concentrations of poly (α1, 3 glucan) was formed. However, while gtfJ can produce poly (α1, 3 glucan) in the absence of the primer dextran, the concentration of the poly (α1, 3 glucan) formed in the reaction mixture, using dialysis tubes and in the presence of the primer dextran, is considerably higher (e.g., 2.50 g) as shown in Table 3.

What is claimed is:

1. A reaction system for producing poly (alpha 1,3 glucan), wherein said reaction system comprises:
   a) a first chamber that comprises an enzyme reaction solution comprising:
      i) sucrose, and
      ii) at least one glucosyltransferase enzyme that is a *Streptococcus salivarius* GtfJ enzyme; and
   b) a second chamber, separated from the first chamber by a semi-permeable membrane that is in contact with the enzyme reaction solution, wherein the semi-permeable membrane is permeable to fructose and sucrose, but impermeable to poly (alpha 1,3 glucan) and the glucosyltransferase enzyme, and wherein the semi-permeable membrane facilitates continuous removal of fructose and other low molecular weight moieties from the first chamber while retaining poly (alpha 1,3 glucan) and the at least one glucosyltransferase enzyme inside the first chamber, wherein the semi-permeable membrane has a molecular weight cut-off from 12,000 to 100,000 Daltons.

2. The reaction system of claim 1, wherein said enzyme reaction solution further comprises at least one primer.

3. The reaction system of claim 1, wherein the glucosyltransferase enzyme is a primer-independent enzyme.

4. The reaction system of claim 1, wherein the semi-permeable membrane facilitates accumulation of poly (alpha 1,3 glucan) in the first chamber to a concentration ranging from 30 grams per liter to 200 grams per liter.

5. The reaction system of claim 4, wherein the semi-permeable membrane is a dialysis tubing.

6. The reaction system of claim 2, wherein the at least one primer is dextran.

7. The reaction system of claim 1, wherein more than one glucosyltransferase enzyme is present in the enzyme reaction solution.

8. The reaction system of claim 7, wherein the more than one glucosyltransferase enzyme comprises a mixture of at least one primer-dependent enzyme and at least one primer-independent enzyme.

9. The reaction system of claim 1, wherein the poly (alpha 1,3 glucan) is a solid.

10. The reaction system of claim 1, wherein the second chamber comprises a sucrose solution.

\* \* \* \* \*